US 9,925,084 B2

(12) United States Patent
Tanaka et al.

(10) Patent No.: US 9,925,084 B2
(45) Date of Patent: Mar. 27, 2018

(54) BODY EXERCISE DEVICE

(71) Applicant: OMRON HEALTHCARE CO., LTD., Muko-shi, Kyoto (JP)

(72) Inventors: Kenshin Tanaka, Kyoto (JP); Hiroshi Ogawa, Kyoto (JP)

(73) Assignee: OMRON CORPORATION, Muko-shi (JP)

( * ) Notice: Subject to any disclaimer, the term of this patent is extended or adjusted under 35 U.S.C. 154(b) by 117 days.

(21) Appl. No.: 14/629,084

(22) Filed: Feb. 23, 2015

(65) Prior Publication Data
US 2015/0173931 A1 Jun. 25, 2015

Related U.S. Application Data

(63) Continuation of application No. PCT/JP2013/071811, filed on Aug. 12, 2013.

(30) Foreign Application Priority Data

Sep. 18, 2012 (JP) ................................. 2012-204440

(51) Int. Cl.
*A63B 21/002* (2006.01)
*A61F 5/04* (2006.01)
(Continued)

(52) U.S. Cl.
CPC ............ *A61F 5/04* (2013.01); *A63B 21/0088* (2013.01); *A63B 21/068* (2013.01); *A63B 22/16* (2013.01);
(Continued)

(58) Field of Classification Search
CPC ............ A63B 21/0085; A63B 21/0088; A63B 23/0238; A63B 23/0244; A63B 24/0062;
(Continued)

(56) References Cited

U.S. PATENT DOCUMENTS 4,634,179 A * 1/1987 Hashimoto ............ A47C 7/467
297/284.3
5,112,045 A * 5/1992 Mason .................... A63B 22/18
482/112
(Continued)

FOREIGN PATENT DOCUMENTS

JP H06-55577 B2 7/1994
JP H06-341912 A 12/1994
(Continued)

OTHER PUBLICATIONS

Definition of Seat, <http://www.thefreedictionary.com/seat>.*
Nov. 5, 2013 International Search Report issued in International Patent Application No. PCT/JP2013/071811.

Primary Examiner — Gregory Winter
(74) Attorney, Agent, or Firm — Oliff PLC

(57) ABSTRACT

A body exercise device includes a seat portion having a seat face, a pair of left and right airbags and a pair of front and rear airbags causing the seat face of the seat portion to be left-right and front-rear inclined, and an air supply unit that supplies pressurized air to the airbags. An air supply/discharge switching unit switches between supplying air to and discharging air from the airbags, and a pressure detection unit detects pressure in the airbags. A balance determination unit, in a process of supplying air to or discharging air from the right and left or front and rear airbags according to the switching operation of the air supply/discharge switching unit, determines the left-right or front-rear balance state of the user based on a difference in pressure change in the pair of left and right airbags or the pair of front and rear airbags.

2 Claims, 14 Drawing Sheets

US 9,925,084 B2
Page 2

(51) Int. Cl.
  *A63B 21/008* (2006.01)
  *A63B 21/068* (2006.01)
  *A63B 22/18* (2006.01)
  *A63B 23/02* (2006.01)
  *A63B 24/00* (2006.01)
  *A63B 22/16* (2006.01)
  *A63B 23/00* (2006.01)
  *A63B 71/06* (2006.01)

(52) U.S. Cl.
  CPC .......... *A63B 22/18* (2013.01); *A63B 23/0238* (2013.01); *A63B 23/0244* (2013.01); *A63B 24/0062* (2013.01); *A63B 24/0087* (2013.01); A63B 2023/006 (2013.01); A63B 2024/0093 (2013.01); A63B 2071/0625 (2013.01); A63B 2071/0652 (2013.01); A63B 2071/0655 (2013.01); A63B 2208/0233 (2013.01); A63B 2220/56 (2013.01); A63B 2225/01 (2013.01); A63B 2225/50 (2013.01); A63B 2225/54 (2013.01)

(58) Field of Classification Search
  CPC ........ A63B 2071/0652; A63B 2225/62; A47C 27/10; A47C 27/083; A61G 7/001; A61G 7/05769; A61G 7/05776
  USPC .......................................... 297/452.41, 284.6
  See application file for complete search history.

(56) References Cited

U.S. PATENT DOCUMENTS

| | | | | |
|---|---|---|---|---|
| 5,170,364 A * | 12/1992 | Gross | ........................ | A47C 4/54 297/284.6 |
| 5,338,276 A | 8/1994 | Jull et al. | | |
| 5,558,398 A * | 9/1996 | Santos | ...................... | A47C 4/54 297/284.3 |
| 5,925,000 A * | 7/1999 | Marciniak | ................ | A43B 7/24 482/8 |
| 6,056,079 A * | 5/2000 | Cech | ...................... | B60N 2/002 177/144 |
| 6,088,642 A * | 7/2000 | Finkelstein | ............ | B60N 2/002 297/284.1 |
| 6,094,762 A * | 8/2000 | Viard | .................. | A61G 7/05769 177/144 |
| 6,154,907 A * | 12/2000 | Cinquin | ............. | A61G 7/05769 5/706 |
| 6,159,172 A * | 12/2000 | Gray | ..................... | A61G 5/1043 297/452.41 |
| 7,074,166 B2 * | 7/2006 | Weitzman | ............ | A61H 9/0078 446/220 |
| 7,811,216 B2 * | 10/2010 | Babiarz | ............... | A63B 21/0085 446/220 |
| 8,147,000 B1 * | 4/2012 | Drake | .................... | A47C 7/021 297/219.1 |
| 2002/0027384 A1 * | 3/2002 | Zur | ...................... | A61G 5/1043 297/452.41 |
| 2006/0258512 A1 * | 11/2006 | Nicolas | .............. | A63B 23/0458 482/52 |
| 2007/0061976 A1 * | 3/2007 | Bazargani | ........... | A47G 9/1027 5/644 |
| 2009/0106905 A1 * | 4/2009 | Ochi | .................... | A47C 27/082 5/713 |
| 2010/0313359 A1 * | 12/2010 | Scott | ................... | A47G 9/1027 5/655.3 |
| 2011/0296622 A1 * | 12/2011 | Hsu | ....................... | A47C 27/082 5/713 |
| 2014/0167463 A1 * | 6/2014 | Sakata | ................. | B60N 2/0244 297/284.3 |
| 2014/0305445 A1 * | 10/2014 | Morimura | .......... | A61G 7/05776 128/889 |

FOREIGN PATENT DOCUMENTS

| JP | H11-56818 A | 3/1999 |
|---|---|---|
| JP | 2002-248144 A | 9/2002 |
| JP | 2010-075622 A | 4/2010 |
| JP | 2011-239824 A | 12/2011 |
| JP | 2012-157580 A | 8/2012 |

\* cited by examiner

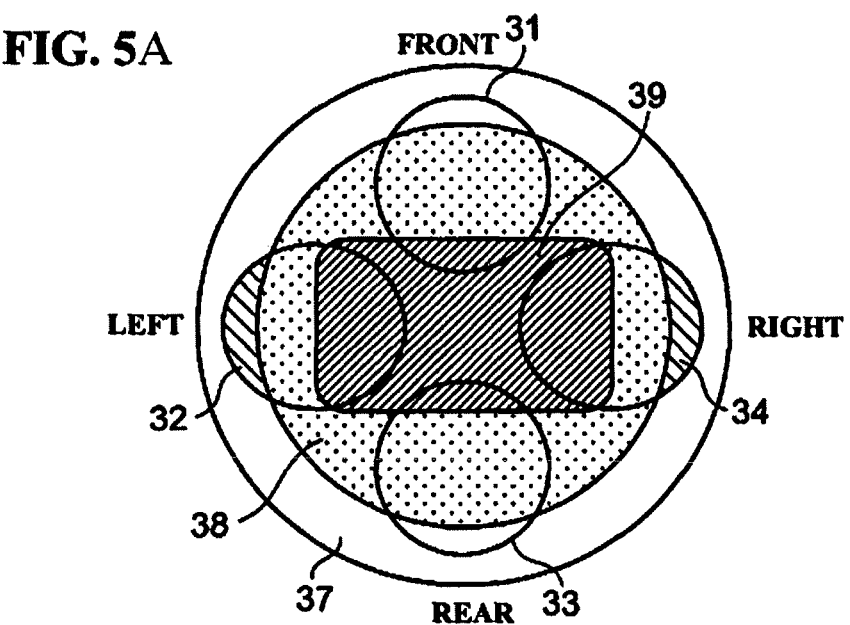
FIG. 5A
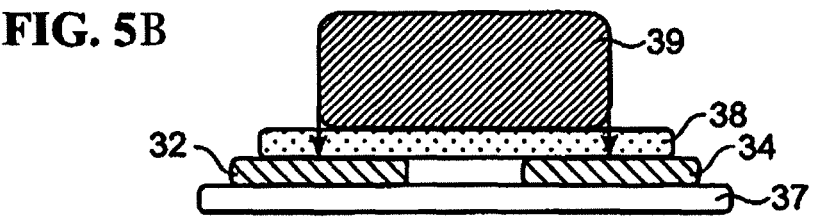
FIG. 5B
FIG. 5C
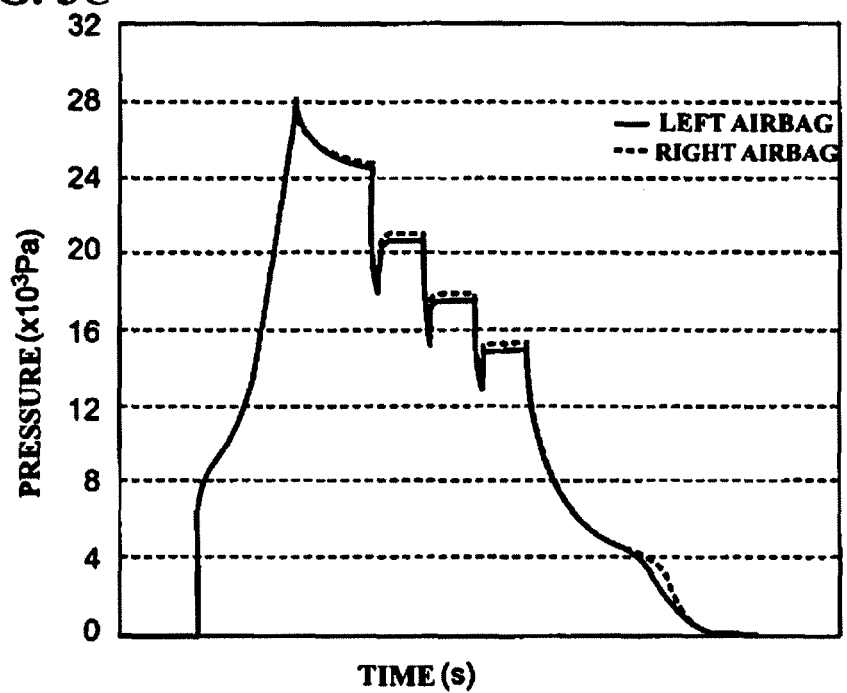

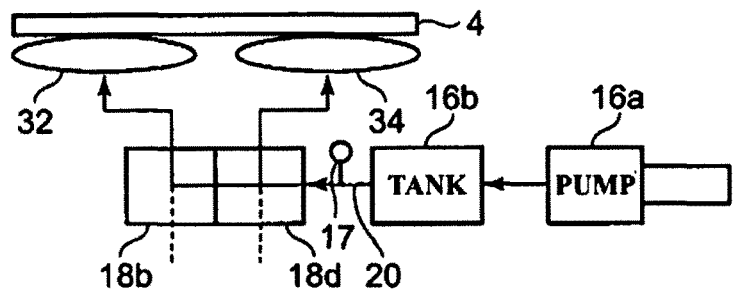
FIG. 9F — 6. PARALLEL AIR SUPPLY
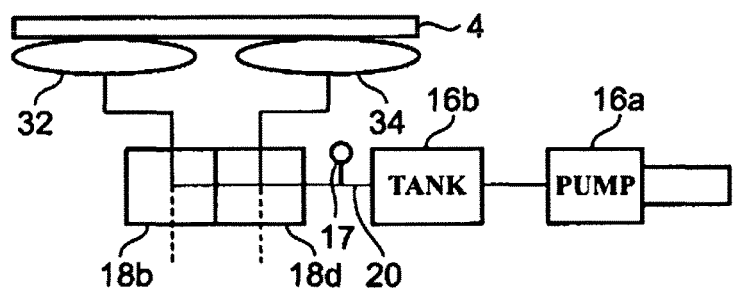
FIG. 9G — 7. STOP SUPPLY OF AIR → HOLD
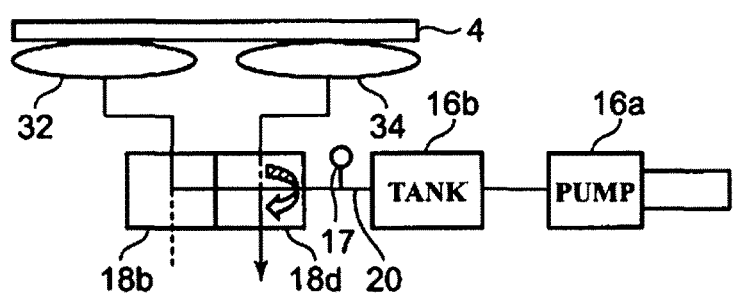
FIG. 9H — 8. DISCHARGE AIR FROM AIRBAG 2
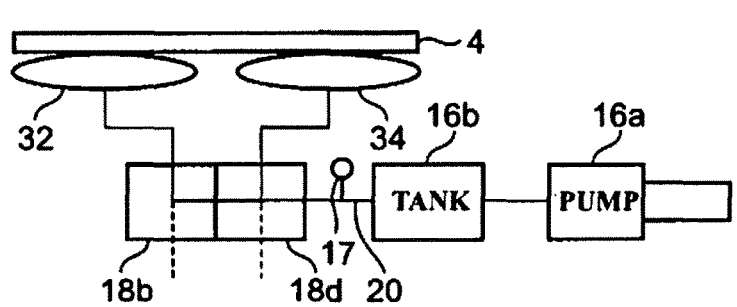
FIG. 9I — 9. STOP DISCHARGE OF AIR → HOLD
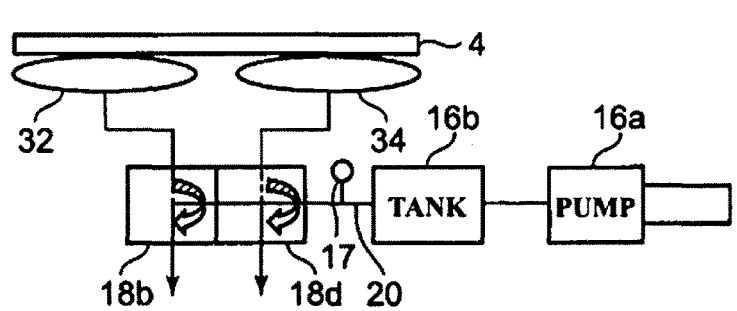
FIG. 9J — 10. PARALLEL AIR DISCHARGE

FIG. 14

| | |
|---|---|
| TO THE LEFT | 1) STRETCH FOR RIGHT ANTERIOR GLUTEUS MEDIUS MUSCLE, RIGHT TENSOR FASCIAE LATAE MUSCLE, AND RIGHT PIRIFORMIS MUSCLE |
| | 2) FACILITATION EXERCISE FOR RIGHT ANTERIOR GLUTEUS MEDIUS MUSCLE, RIGHT TENSOR FASCIAE LATAE MUSCLE, AND RIGHT PIRIFORMIS MUSCLE |
| | 3) RAPID FACILITATION EXERCISE AND ROTATION EXERCISE FOR RIGHT ANTERIOR GLUTEUS MEDIUS MUSCLE, RIGHT TENSOR FASCIAE LATAE MUSCLE, AND RIGHT PIRIFORMIS MUSCLE |
| CENTER | 1) STRETCH FOR ANTERIOR GLUTEUS MEDIUS MUSCLES (LEFT AND RIGHT), TENSOR FASCIAE LATAE MUSCLES (LEFT AND RIGHT), AND PIRIFORMIS MUSCLES (LEFT AND RIGHT) |
| | 2) FACILITATION EXERCISE FOR ANTERIOR GLUTEUS MEDIUS MUSCLES (LEFT AND RIGHT), TENSOR FASCIAE LATAE MUSCLES (LEFT AND RIGHT), AND PIRIFORMIS MUSCLES (LEFT AND RIGHT) |
| | 3) RAPID FACILITATION EXERCISE AND ROTATION EXERCISE FOR ANTERIOR GLUTEUS MEDIUS MUSCLES (LEFT AND RIGHT), TENSOR FASCIAE LATAE MUSCLES (LEFT AND RIGHT), AND PIRIFORMIS MUSCLES (LEFT AND RIGHT) |
| TO THE RIGHT | 1) STRETCH FOR LEFT ANTERIOR GLUTEUS MEDIUS MUSCLE, LEFT TENSOR FASCIAE LATAE MUSCLE, AND LEFT PIRIFORMIS MUSCLE |
| | 2) FACILITATION EXERCISE FOR LEFT ANTERIOR GLUTEUS MEDIUS MUSCLE, LEFT TENSOR FASCIAE LATAE MUSCLE, AND LEFT PIRIFORMIS MUSCLE |
| | 3) RAPID FACILITATION EXERCISE AND ROTATION EXERCISE FOR LEFT ANTERIOR GLUTEUS MEDIUS MUSCLE, LEFT TENSOR FASCIAE LATAE MUSCLE, AND LEFT PIRIFORMIS MUSCLE |

BODY EXERCISE DEVICE

TECHNICAL FIELD

The present invention relates to a body exercise device for performing stretches and exercises for the pelvic area and the periphery of the hip joint of a user.

BACKGROUND ART

Conventionally, there are known to be devices that are provided with multiple airbags in a seat portion on which a user sits, and which allow bodily exercise by causing inflation and contraction of the airbags (e.g., Patent Document 1).

CITATION LIST

Patent Literature

Patent Document 1: JP 2011-239824A

SUMMARY OF INVENTION

Technical Problem

Patent Document 1 discloses a health chair for correcting deviation of the lumbar vertebra or pelvis of a user by controlling the expansion and contraction of multiple airbags provided in a seat face so as to control the inclination of the seat face. However, the health chair disclosed in Patent Document 1 merely includes an inclination means for causing the seat surface to be inclined, and a control means for controlling the inclination of the inclination means, and the health chair causes the user to perform a determined stretch or exercise without regard for what kind of balance state the body of the user is in. In other words, since the health chair disclosed in Patent Document 1 does not detect the balance state of the body of the user, there is a risk of causing the user to perform unsuitable stretches or exercises.

In view of this, it is an object of the present invention to provide a body exercise device configured to detect what kind of balance state the body of the user is in.

Solution to Problem

In order to resolve the foregoing problem, a body exercise device according to the invention includes:

a seat portion having a seat face for a user to sit on;

a pair of left and right airbags and/or a pair of front and rear airbags provided in order to cause the seat surface of the seat portion to be left-right or front-rear inclined;

an air supply unit configured to supply compressed air to the airbags;

an air supply/discharge switching unit configured to switch between supplying air to and discharging air from the airbags;

a pressure detection unit configured to detect pressure in the airbags; and a balance determination unit configured to, in a process of supplying air to or discharging air from the pair of left and right airbags or the pair of front and rear airbags using a switching operation performed by the air supply/discharge switching unit, determine a left-right or front-rear balance of the user based on a difference in pressure change over time in the pair of left and right airbags or the pair of front and rear airbags, detected by the pressure detection unit.

With the body exercise device according to the present invention, in a process of supplying air to or discharging air from the pair of left and right airbags or the pair of front and rear airbags using the air supply/discharge switching unit, the balance determination unit determines the left-right or front-rear balance state of the user based on the difference in pressure change over time in the pair of left and right airbags or the pair of front and rear airbags detected by the detection unit. As a result, it is possible to cause the user to execute a recommended exercise or the like that is suitable for the left-right or front-rear balance state of the user, determined by the balance determination unit.

With the body exercise device according to an embodiment, air-flow resistances of air supply/discharge paths from the airbags to the air supply/discharge switching unit are equal in the pair of left and right airbags or the pair of front and rear airbags.

With the body exercise device according to this embodiment, the load of the user on the pair of left and right airbags or the pair of front and rear airbags is directly reflected in the determination of the balance state, and therefore it is easy for the balance determination unit to determine the left-right or front-rear balance state of the user.

With the body exercise device according to an embodiment, the balance determination unit performs determination such that at least leftward and rightward or frontward and rearward are included as the left-right or front-rear balance states of the user.

With the body exercise device according to this embodiment, balance state determination processing can be performed quickly by determining minimum levels necessary for the left-right or front-rear balance state of the user.

With the body exercise device according to an embodiment, the difference in pressure change over time is a difference in pressure at the elapse of a determined amount of time since starting discharge of air from the airbags.

With the body exercise device according to this embodiment, the difference in pressure of the pair of left and right airbags or the pair of front and rear airbags can be accurately detected, and therefore balance state determination processing can be accurately performed.

With the body exercise device according to an embodiment, the pressure detection unit is provided in each of the airbags.

With the body exercise device according to this embodiment, the pressure in each airbag is directly detected by the individually-provided pressure detection units, and therefore balance state determination processing can be performed rapidly.

With the body exercise device according to an embodiment, only one pressure detection unit is provided so as to be shared by all of the airbags and detects the air pressure of each of the airbags by means of the switching operation performed by the air supply/discharge switching unit.

With the body exercise device according to this embodiment, by using only one pressure detection unit, which is a comparatively high-cost constituent element, it is possible to realize a reduction in cost.

With the body exercise device according to an embodiment, a stretch or exercise corresponding to the result of determination performed by the balance determination unit is presented to the user.

With the body exercise device according to this embodiment, the user is caused to execute a stretch or an exercise that is suitable for the left-right or front-rear balance state of the user, determined by the balance determination unit.

Advantageous Effects of the Invention

As is apparent from the above description, according to the body exercise device of the present invention, it is possible to detect what kind of balance state the body of the user is in. As a result, it is possible to cause the user to execute a stretch or exercise that is suitable for the left-right or front-rear balance state of the user determined by the balance determination unit.

BRIEF DESCRIPTION OF DRAWINGS

FIGS. 5A, 5B and 5C are diagrams for describing a principle of detecting the balance state in the present invention, and are diagrams for a case in which weight is arranged in the center.

FIGS. 9F, 9G, 9H, 9I and 9J are diagrams for describing a method for measuring pressure in multiple airbags using one pressure detection unit.

FIG. 14 shows an example of recommended exercises and the like that are presented to the user.

DESCRIPTION OF EMBODIMENTS

Hereinafter, preferred embodiments of the invention will be described in detail with reference to the drawings.

Figure 1:
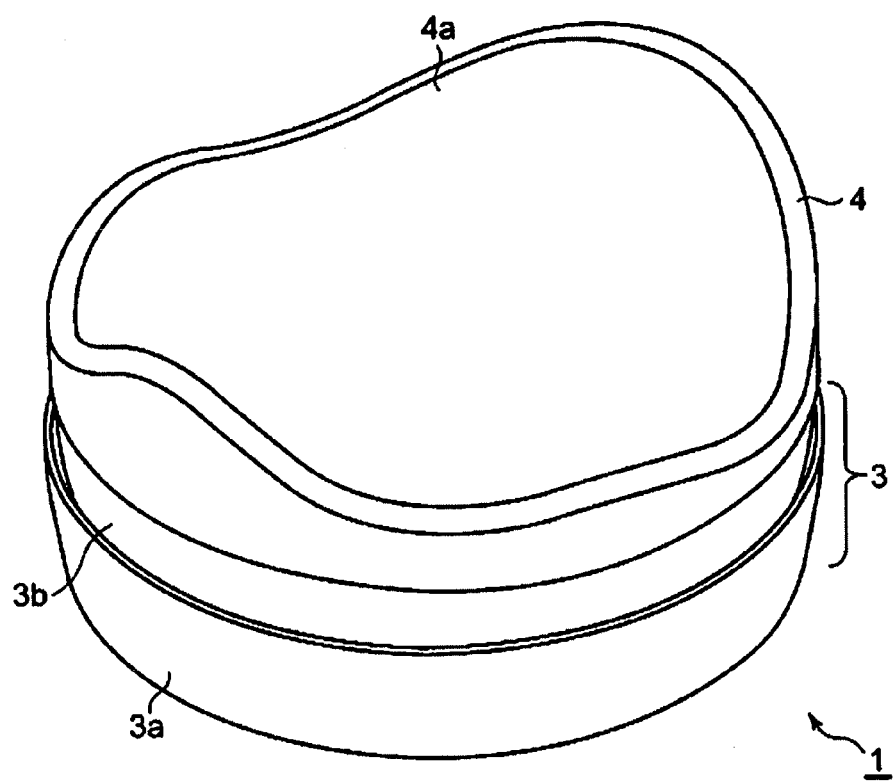
FIG. 1 is a perspective view of the external appearance of a body exercise device according to the present invention.

As shown in FIG. 1, a body exercise device 1 of the present invention is constituted by a roughly circular disc-shaped housing 3 and a roughly circular disc-shaped seat portion 4. The housing 3 is constituted by a lower housing 3a and an upper housing 3b that is configured to be able to swing inside of the lower housing 3a. The seat portion 4 can be mounted on the upper face of the upper housing 3b of the housing 3. The seat portion 4 is entirely constituted by a cushion material having elasticity. The upper face of the seat portion 4 is a curved surface configured to stably support the posterior of a seated user, and functions as the seat face 4a.

Figure 2:
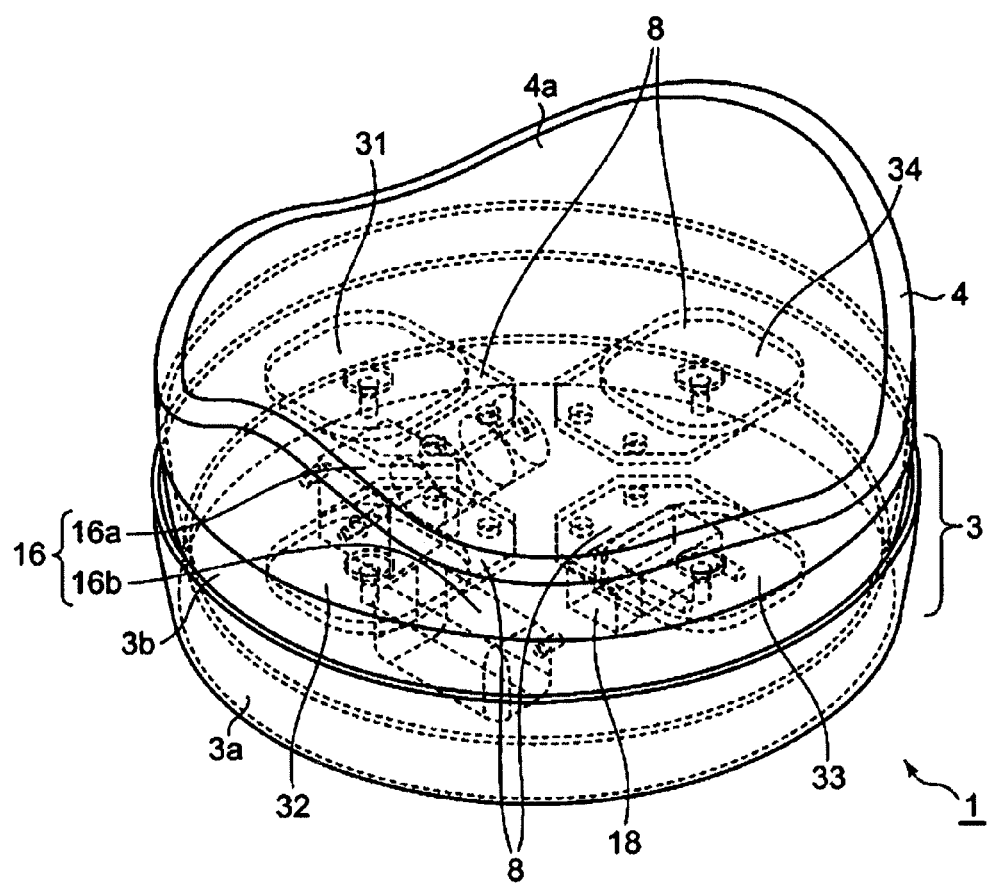
FIG. 2 is a see-through view of the interior of the body exercise device shown in FIG. 1.

As shown in FIG. 2, brackets 8 are fixed at a front side position, left side position, rear side position, and right side position of the upper face of the interior side of the lower housing 3a, and a front airbag 31, a left airbag 32, a rear airbag 33, and a right airbag 34 are attached respectively to the brackets 8. The lower face of the upper housing 3b is supported by the upper face portions of the airbags 31, 32, 33, and 34. The airbags 31, 32, 33, and 34, are bellow-shaped multilayered pouches that can each extend in the upward direction with the supply of air to the pouch interior, and can each contract in a downward direction by discharging the air from the pouch interior. According to the up-down movement of the airbags 31, 32, 33, and 34, the seat face 4a of the seat portion 4 moves up and down and is inclined. The airbags 31, 32, 33, and 34 have air-flow resistances that are substantially equal (have the same shape and internal capacity). Accordingly, the airbags 31, 32, 33, and 34 expand in approximately the same manner with the supply of air, and contract in approximately the same manner with the discharge of air.

As shown in FIG. 2, an air supply unit 16 composed of a pump 16a and a tank 16b, and a three-way switching electromagnetic valve 18 functioning as an air supply/discharge switching unit are provided in the internal space that is surrounded by the inner face of the lower housing 3a and the lower face of the upper housing 3b. A control unit 11, a storage unit 12, a power supply 13, a pressure detection unit 17, and a communication unit 22 are provided in the aforementioned interior space, although these are not shown in FIG. 2. Also, a display unit 14 and an operation unit 15 (not shown) are provided on the side face of the lower housing 3a of the housing 3.

Next, a hardware configuration of the body exercise device 1 will be described with reference to FIG. 3.

Figure 3:
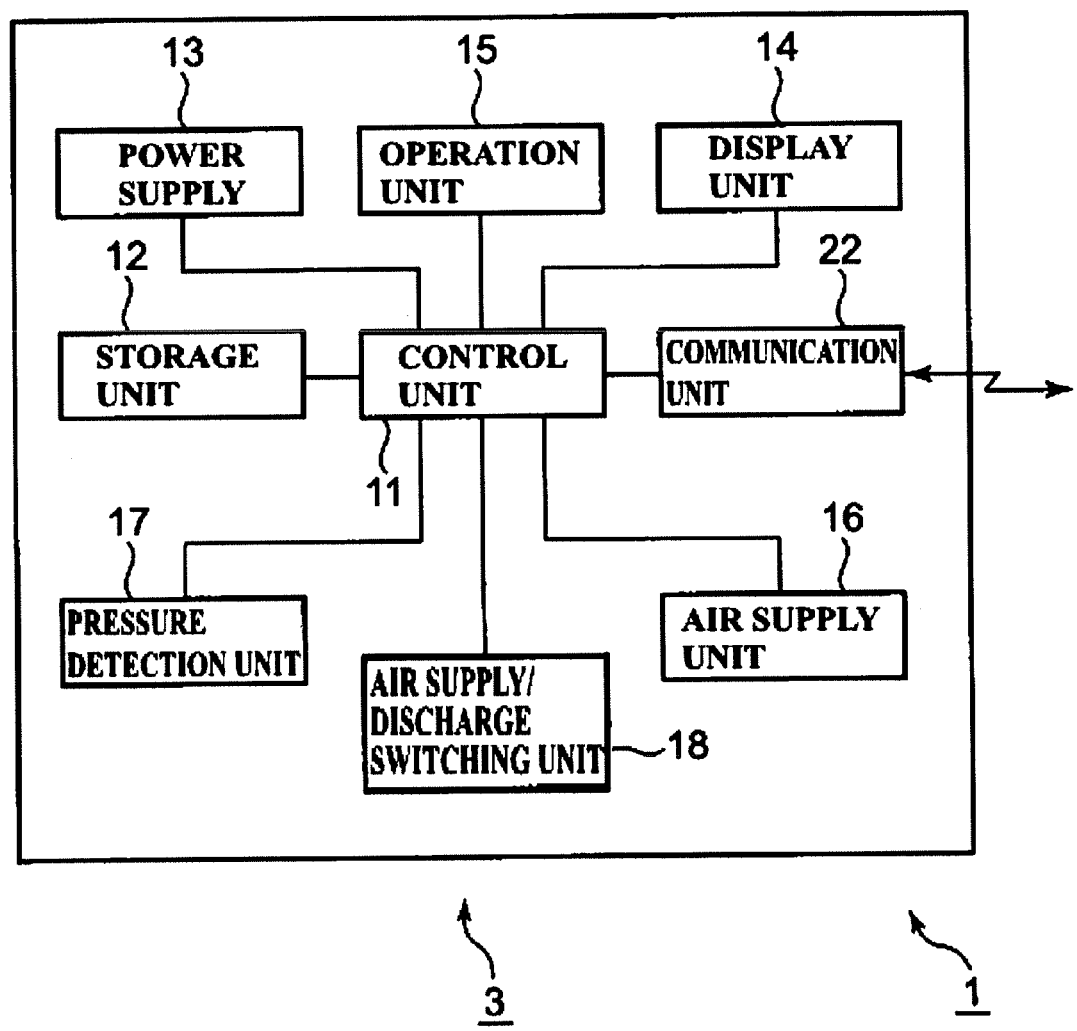
FIG. 3 is a functional block diagram of the body exercise device according to the present invention.

FIG. 3 illustrates the body exercise device 1 as being configured to be usable on a network as well. The body exercise device 1 is configured to be able to mutually communicate over a wire or wirelessly with a server (not shown) via the network (not shown).

As shown in FIG. 2, the housing 3 of the body exercise device 1 includes the control unit 11, the storage unit 12, the power supply 13, the display unit 14, the operation unit 15, the communication unit 22, the air supply unit 16, the pressure detection unit 17, and the air supply/discharge switching unit 18.

The control unit 11 includes a CPU (Central Processing Unit) and auxiliary circuits thereof, controls the parts included in the body exercise device 1, and executes various types of processing in accordance with programs and data stored in the storage unit 12. That is to say, the control unit 11 processes data input from the operation unit 15 and the communication unit 22 and stores the processed data in the storage unit 12, displays it using the display unit 14, causes it to be output from the communication unit 22, and the like.

The control unit 11 performs control of opening and closing the three-way switching electromagnetic valve 18 due to the CPU executing a program. By controlling the opening and closing of the three-way switching electromagnetic valve 18, it is possible to control the supply and discharge of air to and from the pair of left and right airbags 32 and 34 or the pair of front and rear airbags 31 and 33. In the process of controlling the supply and discharge of air to and from the pair of left and right airbags 32 and 34 or the pair of front and rear airbags 31 and 33, the control unit 11 functions as a balance determination unit that determines the left-right or front-rear balance state of the user based on a difference in pressure change over time of the pair of left and right airbags 32 and 34 or the pair of front and rear airbags 31 and 33, which are measured by the pressure sensor 17 functioning as a pressure detection unit.

The control unit 11 functions as a display control unit that controls the display of the determined balance state of the user and content regarding stretches and/or exercises recommended according to the determined balance state (referred to below as "recommended exercises" and the like) on the display unit 14.

The storage unit 12 includes a RAM (Random Access Memory) that is used as a work region needed for executing a program using the control unit 11, and a ROM (Read Only Memory) for storing basic programs to be executed by the control unit 11. Also, it is possible to use a semiconductor memory (memory card, SSD (Solid State Drive)) as a storage medium for an auxiliary storage apparatus for supplementing the storage region of the storage unit 12.

The ROM of the storage unit 12 stores determination references for determining the left-right or front-rear balance state of the user, content of recommended exercises and the like, operation sequences of the air supply/discharge switching unit 18 for causing the user to execute recommended exercises and the like, and display content for the recommended exercises.

For example, the operation unit 15 includes a power supply switch (not shown) that is operated in order to switch on or off the power supply 13 of the body exercise device 1, and an operation switch (not shown) that is operated to select a user in order to store the measurement results for that user in the storage unit 12, or to select any choice among the provided recommended exercises or the like.

The display unit 14 includes a display screen (e.g., display by means of illumination using LEDs, an LCD (Liquid Crystal Display), or an EL (Electroluminescence) display). The display unit 14 displays content such as measurement results and recommended exercises for the user, and the like on the display screen. Control of the display screen is performed by the control unit 11, which functions as a display control unit.

The communication unit 22 is used to transmit data generated by the control unit 11 or data stored in the storage unit 12 to the server via a network, to receive data generated by the control unit (not shown) of the server or data stored in the storage unit (not shown) of the server, and the like. Here, "server" means a normal server, as well as a wider concept including stationary terminals such as personal computers or mobile terminals such as mobile phones, smartphones, PDAs (personal digital assistants), or tablets.

Figure 4:
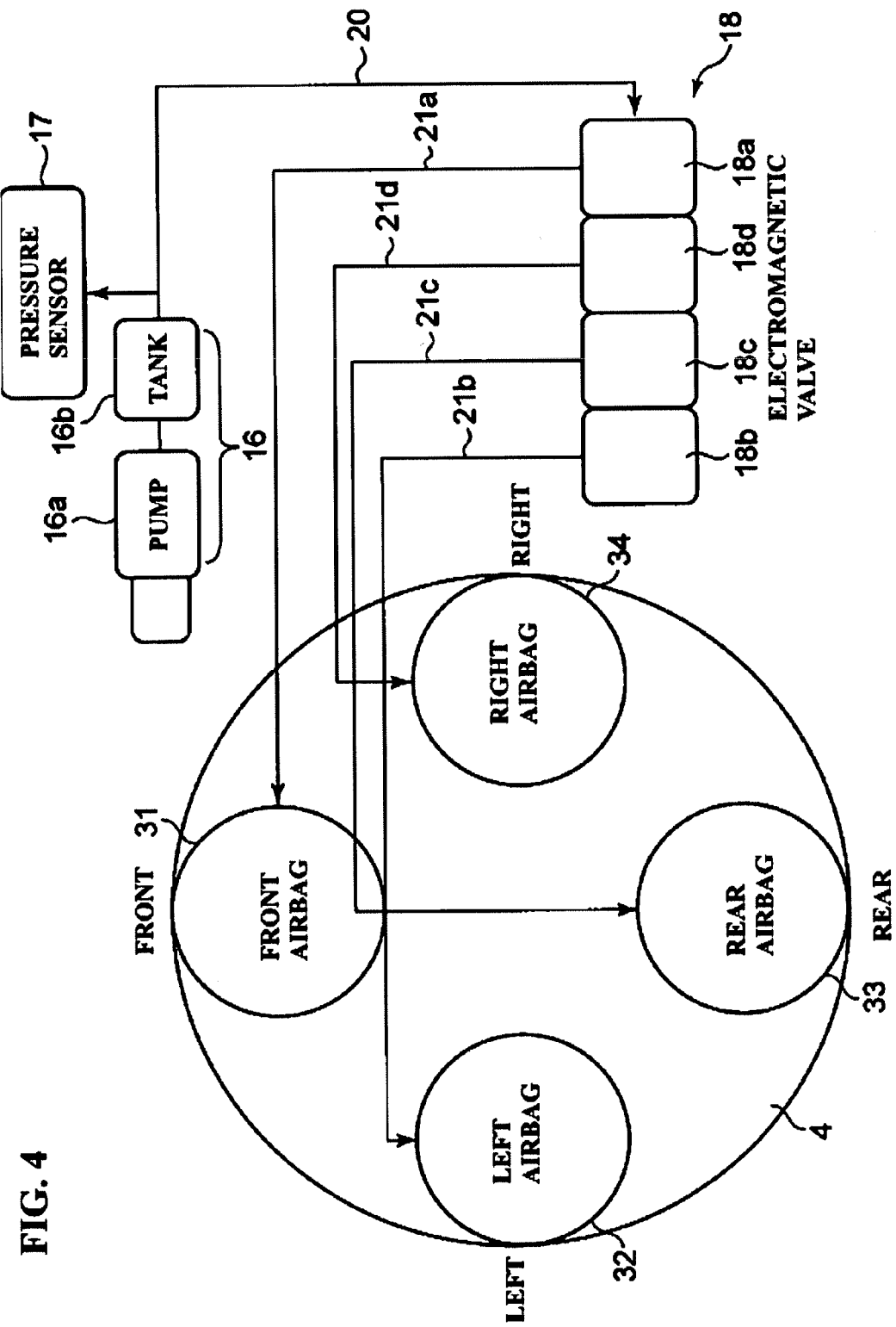
FIG. 4 is a diagram for describing an air control system for the body exercise device according to the present invention.

An example of an air control system of the body exercise device 1 will be described next with reference to FIG. 4. The pump 16a, which creates pressurized air, is connected to the tank 16b, which stores the pressurized air, and thereafter is connected to the main path 20. The pressure sensor 17 functioning as a pressure detection unit is connected to the main path 20, and the pressure in the main path 20 is detected by the pressure sensor 17. The main path 20 is connected to the supply port of the three-way switching electromagnetic valve 18.

The three-way switching electromagnetic valve 18 is constituted by four airbag electromagnetic valves 18a, 18b, 18c, and 18d, or in other words, a front airbag electromagnetic valve 18a, a left airbag electromagnetic valve 18b, a rear airbag electromagnetic valve 18c, and a right airbag electromagnetic valve 18d. The four airbag electromagnetic valves 18a, 18b, 18c, and 18d are controlled using valve control signals from the control unit 11. The airbag electromagnetic valves 18a, 18b, 18c, and 18d have air-flow resistances that are substantially equal (the shapes and opening diameters of ports thereof are the same). Accordingly, the airbag electromagnetic valves 18a, 18b, 18c, and 18d can supply and discharge air in roughly the same manner when supplying air to and discharging air from the airbags 31, 32, 33, and 34.

A front branching path 21a connects the front airbag electromagnetic valve 18a and the front airbag 31. A left branching path 21b connects the left airbag electromagnetic valve 18b and the left airbag 32. A rear branching path 21c connects the rear airbag electromagnetic valve 18c and the rear airbag 33. A right branching path 21d connects the right airbag electromagnetic valve 18d and the right airbag 34. The branching paths 21a, 21b, 21c, and 21d have air-flow resistances that are substantially equal (the lengths and opening diameters of connection piping are the same). Accordingly, the branching paths 21a, 21b, 21c, and 21d can supply and discharge air in roughly the same manner when supplying and discharging air to and from the airbags 31, 32, 33, and 34.

As described above, the airbags 31, 32, 33, and 34 have air-flow resistances that are substantially equal, and the airbag electromagnetic valves 18a, 18b, 18c, and 18d and the branching paths 21a, 21b, 21c, and 21d also have air-flow resistances that are substantially equal. Accordingly, the air supply/discharge paths 21a, 21b, 21c, and 21d that extend from the airbags 31, 32, 33, and 34 to the corresponding airbag electromagnetic valves 18a, 18b, 18c, and 18d have air-flow resistances that are substantially equal.

When an airbag electromagnetic valve (e.g., 18b) among the four airbag electromagnetic valves 18a, 18b, 18c, and 18d is switched to a first position, the airbag (e.g., 32) corresponding to that airbag electromagnetic valve (e.g., 18b) and the tank 16b are connected. Then, when pressurized air is supplied from the tank 16b to the corresponding airbag (e.g., 32), the corresponding airbag (e.g., 32) expands and presses upward on the seat portion 4 located above the corresponding airbag (e.g., 32). When the airbag electromagnetic valve (e.g., 18b) is switched to a second position, the corresponding branching path (e.g., 21b) is blocked, and the state in which the corresponding airbag (e.g., 32) is expanded is maintained. When the airbag electromagnetic valve (e.g., 18b) is switched to a third position, the corresponding airbag (e.g., 32) is connected to the atmosphere so that the air in the corresponding airbag (e.g., 32) is discharged, the corresponding airbag (e.g., 32) contracts, and the seat portion 4 above the corresponding airbag (e.g., 32) lowers. When a later-described recommended exercise or the like is being performed, the above-described expansion operation and contraction operation are performed as necessary in the airbags 31, 32, 33, and 34. Also, the seat portion 4 moves up and down and inclines according to the operations of the airbags 31, 32, 33, and 34.

A principle of detection for detecting the balance state of the user in the body exercise device 1 of this invention will be described below with reference to FIGS. 5 to 7.

Instead of measuring how the pressure changes over time in the pair consisting of the left airbag 32 and the right airbag 34 using the difference in the body balance state of the user, measurement of how the pressure changes over time in the pair consisting of the left airbag 32 and the right airbag 34 when the arrangement of weight 39 is changed with respect to the pair consisting of the left airbag 32 and the right airbag 34 was performed.

A block-shaped weight 39 (e.g., having a weight of 20 kg) is arranged on the left airbag 32 and the right airbag 34 via the disc-shaped support board 38, and the pressure sensor 17 is connected to the left airbag 32 and the right airbag 34. The weight 39 on the left airbag 32 and the right airbag 34 is arranged in a central arrangement, an arrangement to the left, or an arrangement to the right. Also, pressurized air of the same volume is supplied to both the left airbag 32 and the right airbag 34, thereby causing the left airbag 32 and the right airbag 34 to expand. The airbag electromagnetic valves 18b and 18d (not shown) are released at the same time, and thus the expanded left airbag 32 and right airbag 34 discharge the same volume of air at the same time. At this time, measurement of how the pressure changes over time in the left airbag 32 and the right airbag 34 to which the load of the weight 39 was applied is performed.

Figure 6A:
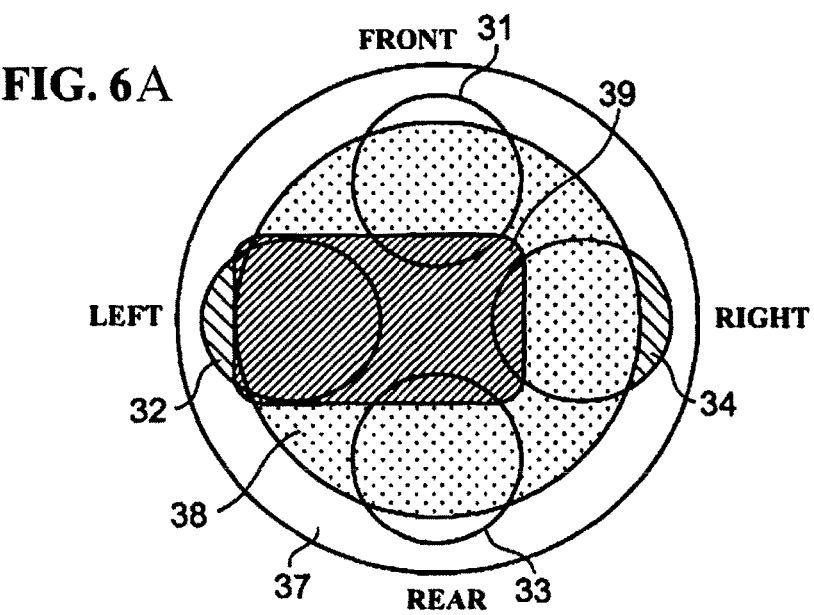
FIGS. 6A, 6B and 6C are diagrams for describing a principle of detecting the balance state in the present invention, and are diagrams for a case in which weight is arranged to the left.
Figure 6B:
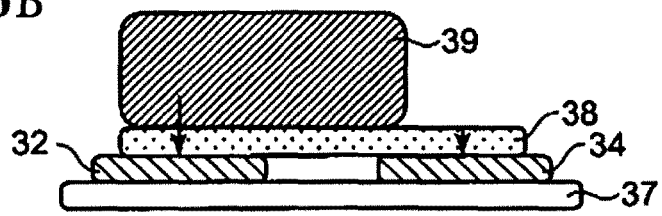
Figure 6C:
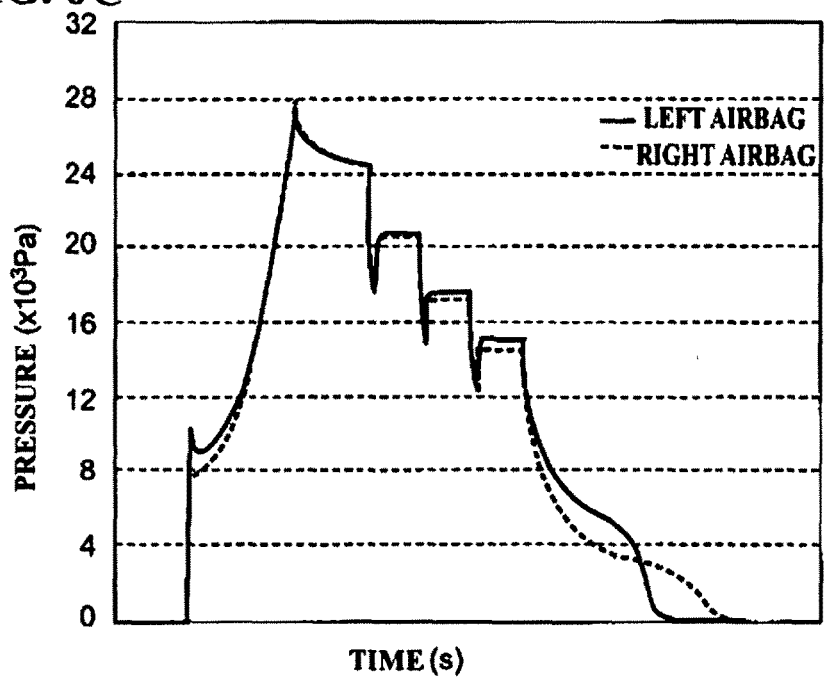
Figure 7A:
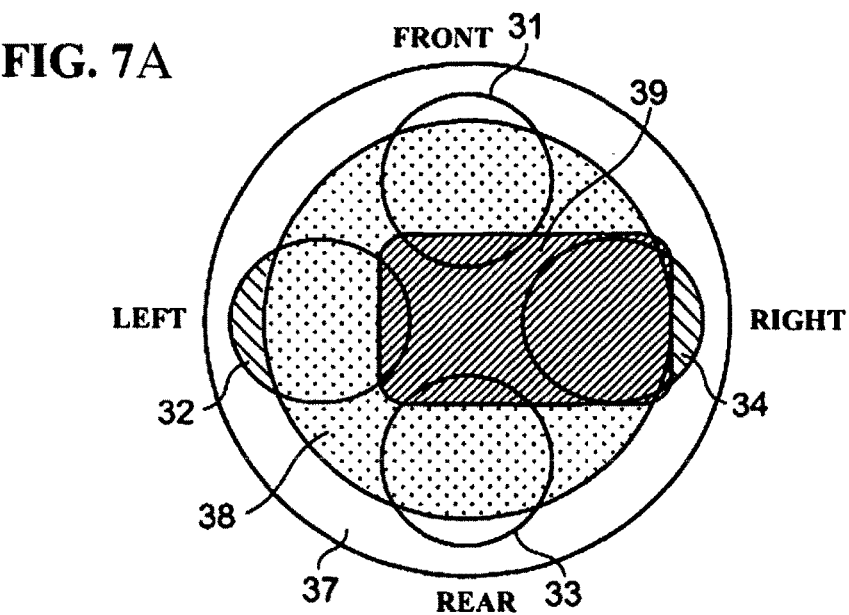
FIGS. 7A, 7B and 7C are diagrams for describing a principle of detecting the balance state in the present invention, and are digrams for a case in which weight is arranged to the right.
Figure 7B:
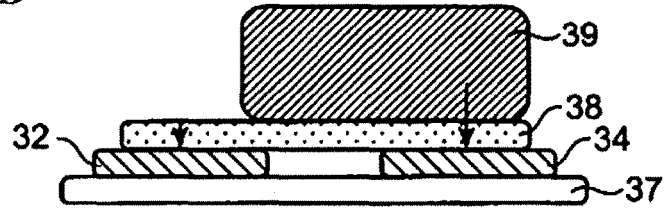
Figure 7C:
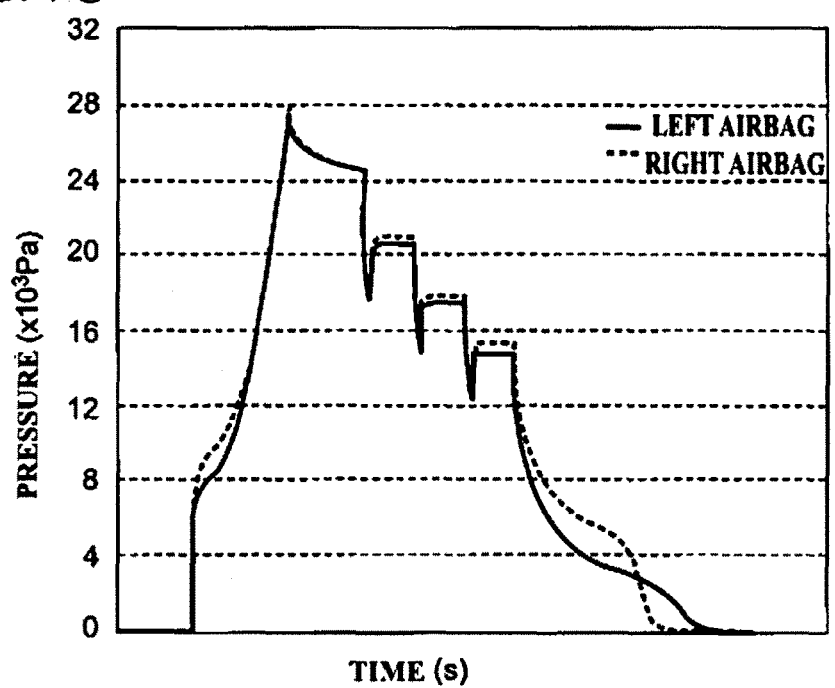

FIG. 5 shows a case in which the weight 39 is in a central arrangement, FIG. 6 shows a case in which the weight 39 is in an arrangement to the left, and FIG. 7 shows a case in which the weight 39 is in an arrangement to the right. In each of FIGS. 5 to 7, (A) is a schematic drawing of a measurement state viewed from above, (B) is a schematic drawing of a measurement state viewed from a side face, and (C) is a diagram showing the measurement result. Note that in FIGS. 5(C), 6(C), and 7(C), the horizontal axis indicates measurement time (units: seconds), and the vertical axis indicates the measured pressure (units: $\times 10^3$ Pa).

As shown in FIG. 5(C), after a pressure of around $28 \times 10^3$ Pa is applied to the left airbag 32 and the right airbag 34, the corresponding airbag electromagnetic valves 18b and 18d are gradually released so as to discharge air, and thereby, after the pressure in the airbags 32 and 34 is gradually lowered, the airbag electromagnetic valves 18b and 18d continue to be released until the pressure is equal to that of the atmosphere.

Since the weight 39 is arranged in the center, it is expected that the pressure change in the left airbag 32 and the pressure change in the right airbag 34 will follow the same locus, but it is thought that FIG. 5(C) reflects the fact that the air-flow resistance in the left airbag 32 and the like and the air-flow resistance in the right airbag 34 and the like are actually slightly different.

FIGS. 6(C) and 7(C) show the weight 39 in an arrangement to the left and an arrangement to the right, respectively. Comparing FIGS. 6(C) and 7(C) gives a result such that the pressures in the left airbag 32 and the right airbag 34 change in different manners during supply of air and discharge of air to and from the pair of left and right airbags 32 and 34.

In FIG. 6(C), when the pressure at the time of supplying air is about $8 \times 10^3$ to about $12 \times 10^3$ Pa, when the pressures at the time of discharging air are held at about $21 \times 10^3$ Pa, about $18 \times 10^3$ Pa, and about $15 \times 10^3$ Pa respectively, and for a short while directly after the airbag electromagnetic valve 18d is continuously released so that the pressure is equal to the atmospheric pressure (about $12 \times 10^3$ Pa to about $3 \times 10^3$ Pa), the pressure of the left airbag 32, which bears more of the load of the weight 39, is higher.

In FIG. 7(C), when the pressure at the time of supplying air is about $8 \times 10^3$ to about $12 \times 10^3$ Pa, when the pressures at the time of discharging air are held at about $21 \times 10^3$ Pa, about $18 \times 10^3$ Pa, and about $15 \times 10^3$ Pa respectively, and for a short while directly after the airbag electromagnetic valve 18b is continuously released so that the pressure is equal to the atmospheric pressure (about $12 \times 10^3$ Pa to about $3 \times 10^3$ Pa), the pressure of the right airbag 34, which bears more of the load of the weight 39, is higher.

In the result of measuring the change in pressure for the arrangement to the left shown in FIG. 6(C), the left airbag 32, which bears more of the load of the weight 39, has the higher pressure. Also, in the result of measuring the change in pressure for the arrangement to the right shown in FIG. 7(C), the right airbag 34, which bears more of the load of the weight 39, has the higher pressure. That is to say that in either case, in the process of supplying air to or discharging air from the pair of left and right airbags 32 and 34, there is a difference in the pressure change, and the airbag that bears more of the load of the weight 39 will have a relatively higher pressure. It is thought that since air is momentarily not supplied to or discharged from the airbags 32 and 34 and the like due to the existence of air-flow resistances in the airbags 32 and 34 and the like, even when pressurized air with the same volume is supplied to or discharged from the left and right airbags 32 and 34, the pressure in the airbag on the side bearing more of the load of the weight 39 will be consequently higher due to the effect of the load of the weight 39 and the application of pressure.

Accordingly, by detecting the difference in the change in pressure over time in the pair of left and right airbags 32 and 34 both when air is being supplied and when air is being discharged, it is possible to detect whether the weight 39 deviates more toward the left or the right, and the deviation detection principle can be applied also to the determination of the body balance state of the user.

A method of measuring the pressure in the pair of left and right airbags 32 and 34 using one pressure sensor 17 in the body exercise device 1 of this invention will be described next with reference to FIGS. 8 and 9.

As shown in FIGS. 8 and 9, one pressure sensor 17 is connected to the main path 20 between the three-way switching electromagnetic valve 18 and the tank 16b. The left airbag electromagnetic valve 18b and the right airbag electromagnetic valve 18d of the three-way switching electromagnetic valve 18 are used to supply air to or discharge air from the left and right airbags 32 and 34. Note that as described above, the left airbag electromagnetic valve 18b and the right airbag electromagnetic valve 18d are configured such that the left and right airbags 32 and 34 and the tank 16b are connected in the first position, the branching paths 21b and 21d are blocked in the second position, and the left and right airbags 32 and 34 and the atmosphere are connected in the third position.

Figure 8A:
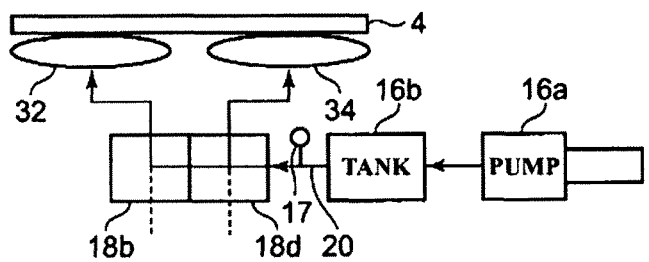
FIGS. 8A, 8B, 8C, 8D and 8E are diagrams for describing a method for measuring pressure in multiple airbags using one pressure detection unit.

First, in FIG. 8(A), the left airbag electromagnetic valve 18b and the right airbag electromagnetic valve 18d are switched to the first position, and the pressurized air stored in the tank 16b is supplied to both the left and right airbags 32 and 34 so that the left and right airbags 32 and 34 expand (parallel air supply). The pressure in the process of supplying air to the left and right airbags 32 and 34 is measured by the pressure sensor 17.

Figure 8B:
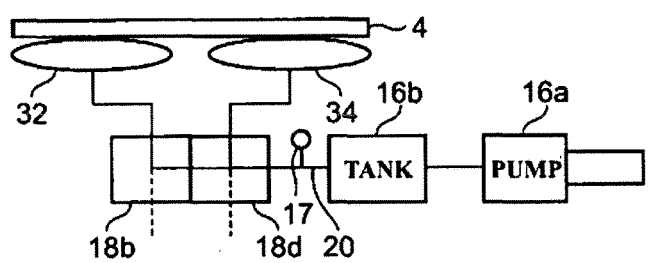

In FIG. 8(B), the left airbag electromagnetic valve 18b and the right airbag electromagnetic valve 18d are switched to the second position, and the expanded state of the left and right airbags 32 and 34 is held for a predetermined amount of time (e.g., 3 to 4 seconds) (air supply stopping and holding). The pressure at the time of expanding and holding the left and right airbags 32 and 34 is measured by the pressure sensor 17.

Figure 8C:
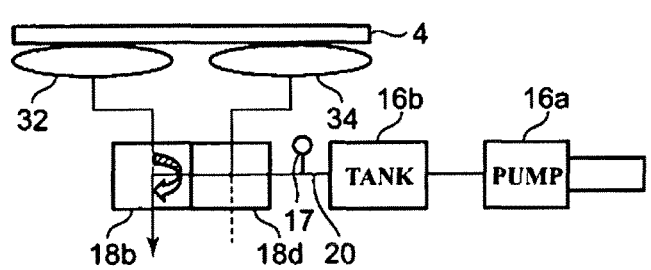

In FIG. 8(C), only the left airbag electromagnetic valve 18b is switched to the third position, and the pressurized air in the left airbag 32 is discharged to the atmosphere so that the left airbag 32 contracts (discharge of air from the left airbag). The pressure in the process of discharging the air from the left airbag 32 is measured by the pressure sensor 17.

Figure 8D:
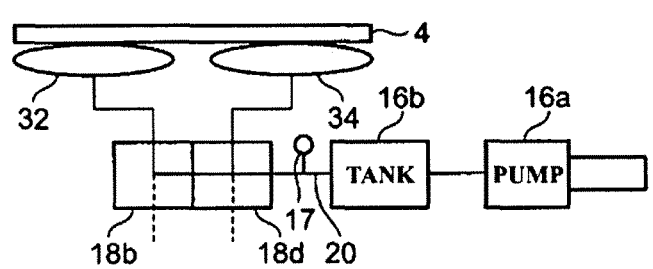

In FIG. 8(D), upon the elapse of a predetermined amount of time (e.g., 3 to 4 seconds) since the start of the discharge of air from the left airbag 32, the left airbag electromagnetic valve 18b is switched to the second position, and the left and right airbags 32 and 34 are held for a predetermined amount of time (e.g., 3 to 4 seconds) (stopping discharge of air and holding the left airbag 32). The pressure while holding for a predetermined amount of time after the discharge of air from the left airbag 32 is measured by the pressure sensor 17.

Figure 8E:
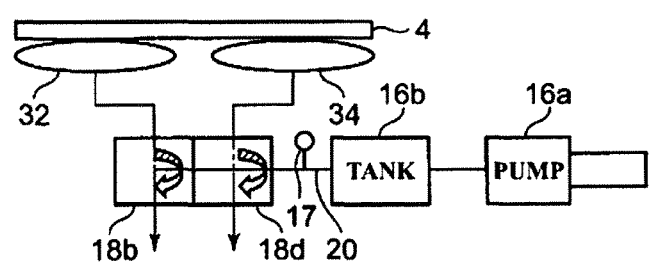

In FIG. 8(E), both the left airbag electromagnetic valve 18b and the right airbag electromagnetic valve 18d are switched to the third position, the pressurized air in the left airbag 32 and right airbag 34 is discharged until the pressure thereof is equal to the atmospheric pressure, and the left airbag 32 and right airbag 34 contract (parallel air discharge). The pressure in the process of atmospheric release of the left and right airbags 32 and 34 is measured by the pressure sensor 17.

Next, in FIG. 9(F), the left airbag electromagnetic valve 18b and the right airbag electromagnetic valve 18d are switched to the first position, and the pressurized air stored in the tank 16b is supplied to both the left and right airbags 32 and 34 so that the left and right airbags 32 and 34 expand (parallel air supply). The pressure in the process of supplying air to the left and right airbags 32 and 34 is measured by the pressure sensor 17.

In FIG. 9(G), the left airbag electromagnetic valve 18b and the right airbag electromagnetic valve 18d are switched to the second position, and the expanded state of the left and right airbags 32 and 34 is held for a predetermined amount of time (e.g., 3 to 4 seconds) (stopping air supply and holding). The pressure at the time of expanding and holding the left and right airbags 32 and 34 is measured by the pressure sensor 17.

In FIG. 9(H), only the right airbag electromagnetic valve 18d is switched to the third position, and the pressurized air in the right airbag 34 is discharged into the atmosphere so that the right airbag 34 contracts (discharge of air from right airbag). The pressure in the process of discharging the air from the right airbag 34 is measured by the pressure sensor 17.

In FIG. 9(I), upon the elapse of a predetermined amount of time (e.g., 3 to 4 seconds) since the start of the discharge of air from the right airbag 34, the right airbag electromagnetic valve 18d is switched to the second position, and the left and right airbags 32 and 34 are held for a predetermined amount of time (e.g., 3 to 4 seconds) (stopping air discharge from the right airbag 34 and holding). The pressure while holding for a predetermined amount of time after the discharge of air from the right airbag 34 is measured by the pressure sensor 17.

In FIG. 9(J), both the left airbag electromagnetic valve 18b and the right airbag electromagnetic valve 18d are switched to the third position, the pressurized air in the left airbag 32 and right airbag 34 is discharged until the pressure thereof is equal to the atmospheric pressure, and the left airbag 32 and right airbag 34 contract (parallel air discharge). The pressure in the process of atmospheric release of the left and right airbags 32 and 34 is measured by the pressure sensor 17.

With the above-described pressure measurement method, the average pressures of the left and right airbags 32 and 34 are measured using the one pressure sensor 17 connected to the main path 20, and therefore the pressures of the left and right airbags 32 and 34 cannot be measured directly. However, in FIG. 8(D), a pressure in which the discharge of air from the left airbag 32 is reflected is measured, and in FIG. 9(I), a pressure in which the discharge of air from the right airbag 34 is reflected is measured, and therefore the pressure of the left airbag 32 and the pressure of the right airbag 34 are measured indirectly. Accordingly, the pressure values obtained when the operations shown in FIGS. 8(D) and 9(I) are performed can be used as a pressure relating to the discharge of air from the left airbag 32 and a pressure relating to the discharge of air from the right airbag 34. In this way, by performing pressure measurement for multiple airbags using only one pressure sensor 17, which is a part with a relatively high cost, it is possible to realize a lower cost.

Note that it is also possible to provide a pressure sensor 17 separately for each of the airbags 31, 32, 33, and 34. In this case, the pressures of the airbags 31, 32, 33, and 34 are directly detected in parallel at the same time, and therefore balance state determination processing can be performed quickly.

A method of measuring the pressure in the pair of left and right airbags 32 and 34 using one pressure sensor 17 and determining the left-right body balance state of the user based on the measurement result will be described next with reference to FIGS. 10 to 13.

Figure 10:
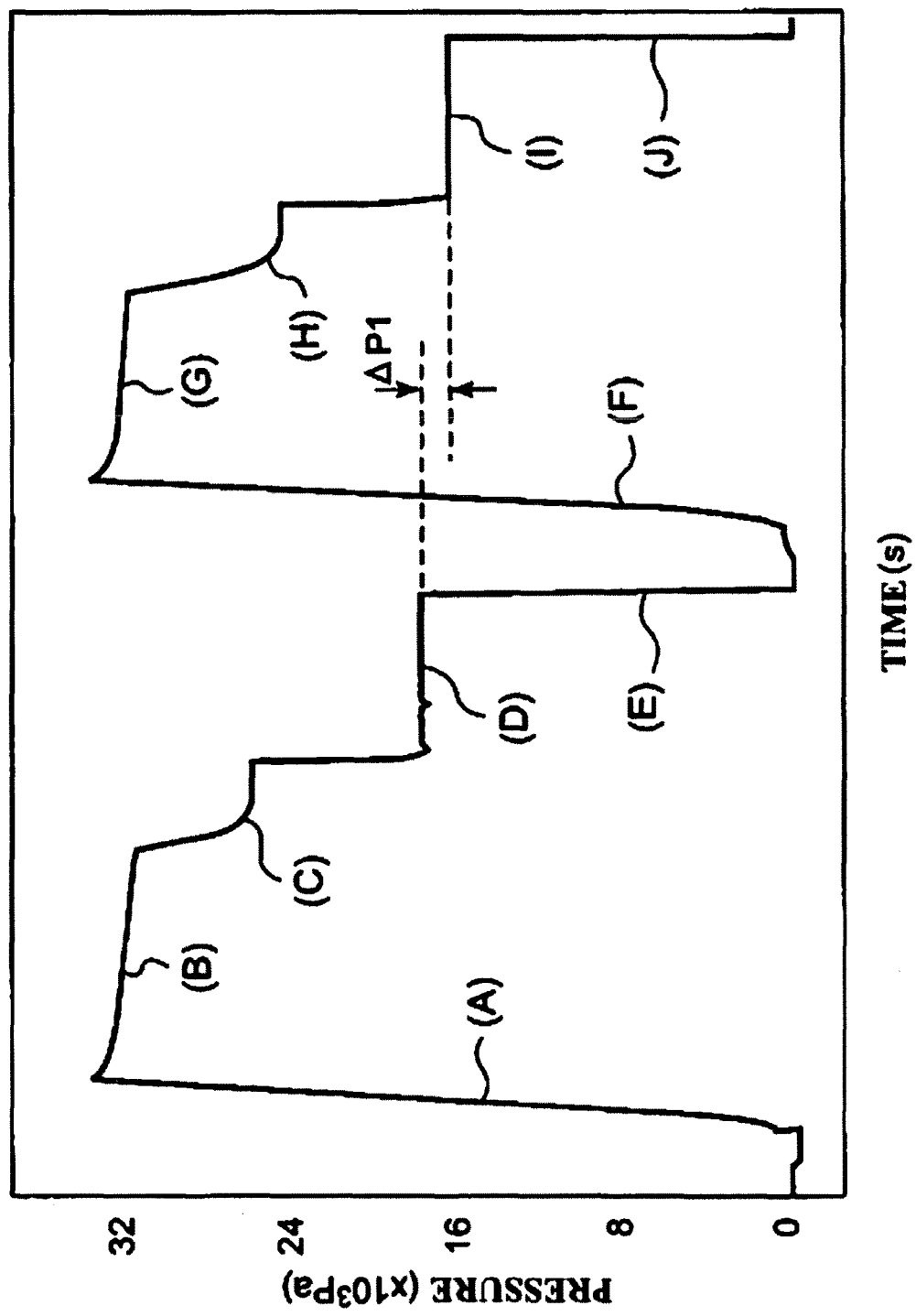
FIG. 10 is a diagram showing a pressure measurement result in the case where there is no deviation in balance when the pressures of a pair of left and right airbags are measured using the methods shown in FIGS. 8 and 9.
Figure 11:
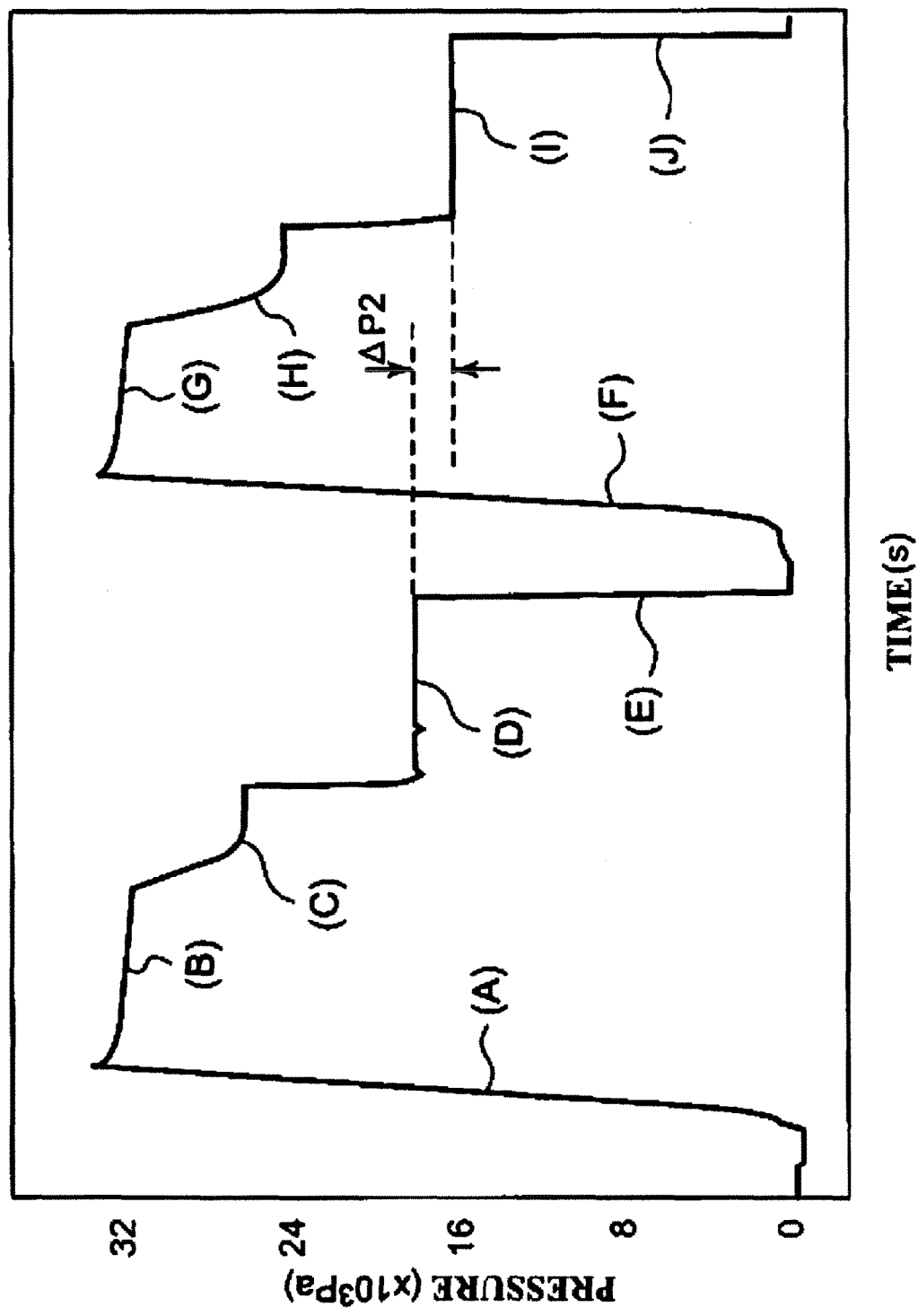
FIG. 11 is a diagram showing a pressure measurement result in the case where the balance deviates to the left when the pressures of a pair of left and right airbags are measured using the methods shown in FIGS. 8 and 9.
Figure 12:
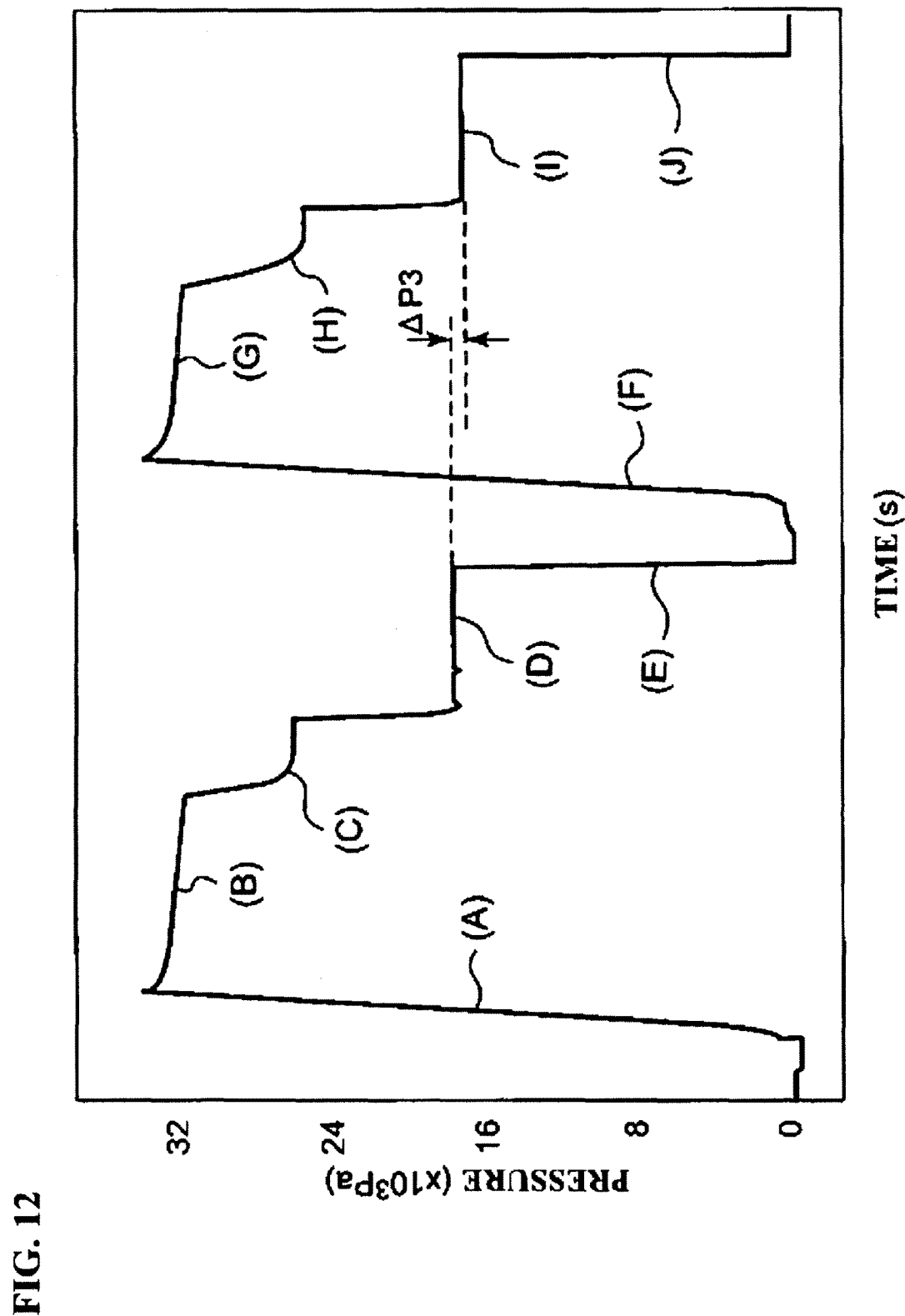
FIG. 12 is a diagram showing a pressure measurement result in the case where the balance deviates to the right when the pressures of a pair of left and right airbags are measured using the methods shown in FIGS. 8 and 9.

FIGS. 10 to 12 show results of using the one pressure sensor 17 to measure the pressure change over time in the left and right airbags 32 and 34 when multiple users in different body balance states in the left-right direction sit on the seat face 4a of the seat portion 4 of the body exercise device 1. In FIGS. 10 to 12, the horizontal axis indicates measurement time (units: seconds), the vertical axis indicates measured pressure (units: $\times 10^3$ Pa). FIG. 10 corresponds to a user who is balanced in the left-right direction, FIG. 11 corresponds to a user whose balance deviates to the left side, and FIG. 12 corresponds to a user whose balance deviates to the right side. Note that (A) to (J) in FIGS. 10 to 12 correspond to the operations in FIGS. 8(A) to 8(E) and FIGS. 9(F) to 9(J).

In FIG. 10, the left chart relates to the pressure change in the left airbag 32 and the right chart relates to the pressure change in the right airbag 34. The letter (D) in this diagram corresponds to FIG. 8(D), or in other words, the operation for stopping discharge of air from the left airbag 32 and holding, and the pressure at that time is the pressure relating to the discharge of air from the left airbag 32, which will be called "left airbag air discharge pressure" for convenience. Also, (I) in this diagram corresponds to FIG. 9(I), or in other words, the operation for stopping discharge of air from the right airbag 34 and holding, and the pressure at this time is the pressure relating to the discharge of air from the right airbag 34, which will be called "right airbag air discharge pressure" for convenience. The left airbag air discharge pressure is greater than the right airbag air discharge pressure, and when the difference in pressure ($\Delta P_1$) between the two is calculated, the result is about $1.44 \times 10^3$ Pa. Since FIG. 10 is the measurement result for the user who is balanced in the left-right direction, it is expected that, ideally, there is no pressure difference between the left airbag air discharge pressure and the right airbag air discharge pressure and the pressure difference ($\Delta P_1$) is zero. However, as described above, even with the user who has balance in the left-right direction, in actuality, a slight difference exists which is caused by non-uniformity in the air-flow resistances of the airbags and the like. In contrast, regarding the user who is balanced in the left-right direction, if the air-flow resistances in the airbags and the like are completely uniform, the pressure difference ($\Delta P_1$) will be zero.

FIG. 11 shows the measurement results for the user whose balance deviates to the left side. In FIG. 11 as well, similarly to FIG. 10 above, the left airbag air discharge pressure at (D) in the diagram is greater than the right airbag air discharge pressure at (I) in the diagram, and when the pressure difference ($\Delta P_2$) between the two is calculated, the result is about $2.22 \times 10^3$ Pa.

FIG. 12 shows the measurement results for the user whose balance deviates to the right side. In FIG. 12 as well, similarly to FIG. 10 above, the left airbag air discharge pressure at (D) in the diagram is greater than the right airbag air discharge pressure at (I) in the diagram, and when the pressure difference ($\Delta P_3$) between the two is calculated, the result is about $0.55 \times 10^3$ Pa.

Upon plotting the pressure differences $\Delta P_1$, $\Delta P_2$, and $\Delta P_3$ between the left airbag air discharge pressure and the right airbag air discharge pressure obtained using FIGS. 10 to 12, FIG. 13 is obtained. As is evident from FIG. 13, the pressure differences $\Delta P_2$, $\Delta P_1$, and $\Delta P_3$ are plotted on a straight line with the measurement result $\Delta P_1$ for the user who is balanced in the left-right direction in the center. Accordingly, using the pressure difference $\Delta P$ between the left airbag air discharge pressure and the right airbag air discharge pressure, it can be determined whether the user is balanced in the left-right direction, the balance deviates to the left side, or the balance deviates to the right side. For example, in the case of FIG. 13, if the pressure difference $\Delta P$ is greater than about $1.8 \times 10^3$ Pa, it can be determined that the balance deviates to the left side. If the pressure difference $\Delta P$ is less than about $1.0 \times 10^3$ Pa, it can be determined that the balance deviates to the right side. If the pressure difference $\Delta P$ is between about $1.0 \times 10^3$ Pa and about $1.8 \times 10^3$ Pa, it can be determined that the user is balanced in the left-right direction.

A menu regarding recommended exercises and the like such as those illustrated in FIG. 14 is stored in the storage unit 12 of the body exercise device 1. That is to say that the ROM of the storage unit 12 stores a menu for a person whose balance deviates to the left side, a menu for a person who is balanced in the left-right direction, and a menu for a person whose balance deviates to the right side. In the example shown in FIG. 14, each menu has three choices.

The control unit 11 functions as a recommended exercise presentation unit for presenting, to the user, a menu of suitable recommended exercises and the like according to the determination result obtained regarding the balance state of the user. For example, the control unit 11 functions as a display control unit that performs control so as to display multiple choices for the corresponding menu on the display unit 14. For example, when it is determined that the balance state of the user deviates to the left side, the following is displayed on the display unit 14: "To the left: 1) Stretch for right anterior gluteus medius muscle, right tensor fasciae latae muscle, and right piriformis muscle".

The user operates the operation buttons of the operation unit 15 so as to select one of the choices displayed on the display unit 14. The control unit 11 controls the switching operation of the three-way switching electromagnetic valve 18 and controls the operations for expanding and contracting the airbags 31, 32, 33, and 34, and thereby the seat portion 4 moves up and down and is inclined according to the selected content of the menu. Accordingly, when the user sits on the seat portion 4, the left-right balance state of the user is determined by the control unit 11 functioning as the balance determination unit. As a result, it is possible to cause the user to execute suitable recommended exercises and the like according to the left-right balance state.

As described above, according to the body exercise device 1 of this invention, in a process in which air is supplied to or discharged from the pair of left and right airbags 32 and 34 according to the switching operation of the three-way switching electromagnetic valve 18 functioning as the air supply/discharge switching unit, the control unit 11 functioning as the balance determination unit can determine the left-right balance state of the user based on the difference in the pressure change over time of the pair of left and right airbags 32 and 34, detected by the pressure sensor 17. As a result, it is possible to cause the user to execute suitable recommended exercises and the like according to the left-right balance state of the user, determined by the control unit 11.

Figure 13:
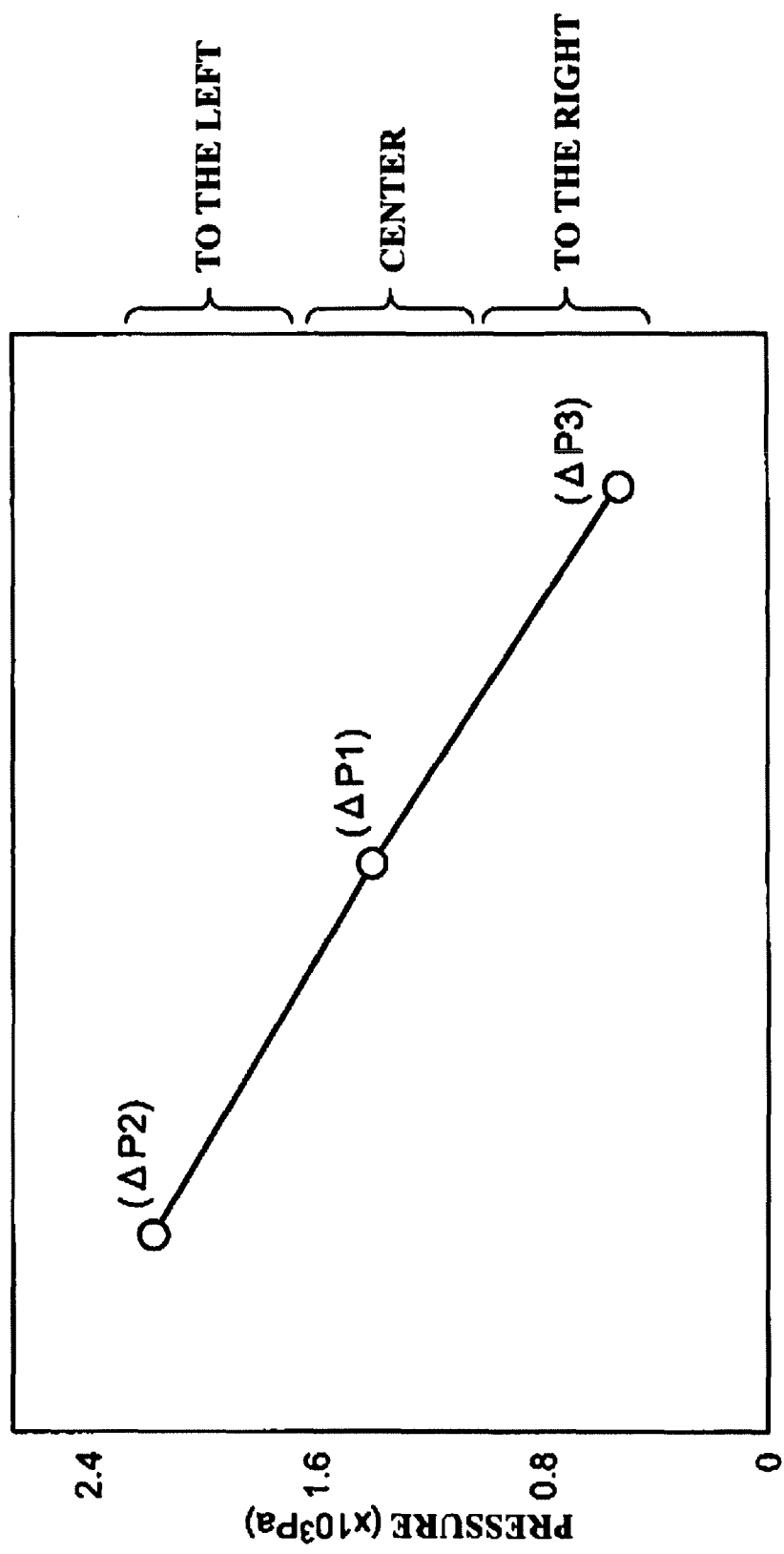
FIG. 13 is a diagram for describing a method for determining deviation in the balance state based on a pressure measurement result in FIGS. 10 to 12.

Note that the determination in FIG. 13 is constituted by three determinations, namely "balance deviates to the left side", "balanced in the left-right direction", and "balance deviates to the right side". However, by using a finer range of numeric values used as determination references shown in FIG. 13, five settings are possible, namely "balance deviates significantly to the left side", "balance deviates a little to the left side", "balanced in the left-right direction", "balance deviates a little to the right side", and "balance deviates significantly to the right side". Also, it goes without saying that the number of determinations by the control unit 11 can be further increased.

Also, regarding the balance state of the user that is to be determined and the airbag and electromagnetic valve and the like that are to be used to detect the difference in the pressure change over time, a description was given for the case of the left-right direction. However, since the description can similarly apply to the case of the front-rear direction, the foregoing description can be read replacing "left-right" with "front-rear".

The above-described embodiments and the numeric values and the like used therein are examples for facilitating understanding of the invention and are not intended to be interpreted as being limiting. The technical scope of the invention is to be defined by the claims.

REFERENCE SIGNS LIST

1 Body exercise device
3 Housing
4 Seat portion
4a Seat face
8 Bracket
11 Control unit (balance determination unit)
12 Storage unit
13 Power supply
14 Display unit
15 Operation unit
16 Air supply unit
16a Pump
16b Tank
17 Pressure sensor (pressure detection unit)
18 Three-way switching electromagnetic valve (air supply/discharge switching unit)
20 Main path
31 Front airbag
32 Left airbag 33 Rear airbag
34 Right airbag

The invention claimed is:

1. A body exercise device comprising:
a seat portion having a seat surface for a user to sit on;
a pair of left and right airbags and a pair of front and rear airbags provided such that the pair of left and right airbags are located on left and right sides with respect to a center of the seat surface and that the pair of front and rear airbags are located on front and rear sides with respect to the center of the seat surface in order to cause the seat surface of the seat portion to be inclinable in a left-right direction and/or in a front-rear direction;
an air supply unit configured to supply compressed air to the pair of left and right airbags and the pair of front and rear airbags;
an air supply and discharge switching unit configured to switch between supplying air to and discharging air from the pair of left and right airbags and the pair of front and rear airbags;
a pressure detection unit configured to detect pressure in the pair of left and right airbags and the pair of front and rear airbags; and
a balance determination unit configured to, in a process of supplying air to or discharging air from the pair of left and right airbags or the pair of front and rear airbags using a switching operation performed by the air supply and discharge switching unit, determine a left-right balance state or a front-rear balance state of the user based on a difference in pressure change over time in the pair of left and right airbags or the pair of front and rear airbags, detected by the pressure detection unit,
wherein stretches and/or exercises that correspond to a result of determination performed by the balance determination unit are output to the user by a display.

2. A body exercise device comprising:
a seat portion having a seat surface for a user to sit on;
a pair of left and right airbags and a pair of front and rear airbags provided such that the pair of left and right airbags are located on left and right sides with respect to a center of the seat surface and that the pair of front and rear airbags are located on front and rear sides with respect to the center of the seat surface in order to cause the seat surface of the seat portion to be inclinable in a left-right direction and/or in a front-rear direction;
an air supply unit configured to supply compressed air to the pair of left and right airbags and the pair of front and rear airbags;
an air supply and discharge switching unit configured to switch between supplying air to and discharging air from the pair of left and right airbags and the pair of front and rear airbags;
a pressure detection unit configured to detect pressure in the pair of left and right airbags and the pair of front and rear airbags; and
a balance determination unit configured to, in a process of supplying air to or discharging air from the pair of left and right airbags or the pair of front and rear airbags using a switching operation performed by the air supply and discharge switching unit, determine a left-right balance state or a front-rear balance state of the user based on a difference in pressure change over time in the pair of left and right airbags or the pair of front and rear airbags, detected by the pressure detection unit,
wherein stretches and/or exercises that correspond to a result of determination performed by the balance determination unit are presented to the user.

* * * * *